(12) United States Patent
Kang

(10) Patent No.: US 12,242,097 B2
(45) Date of Patent: Mar. 4, 2025

(54) OPTICAL TRANSFER DEVICE FOR TISSUE TREATMENT

(71) Applicant: PUKYONG NATIONAL UNIVERSITY INDUSTRY-UNIVERSITY COOPERATION FOUNDATION, Busan (KR)

(72) Inventor: Hyun Wook Kang, Busan (KR)

(73) Assignee: PUKYONG NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 0 days.

(21) Appl. No.: 17/776,436

(22) PCT Filed: Mar. 23, 2022

(86) PCT No.: PCT/KR2022/004050
§ 371 (c)(1),
(2) Date: May 12, 2022

(87) PCT Pub. No.: WO2022/265193
PCT Pub. Date: Dec. 22, 2022

(65) Prior Publication Data
US 2024/0134104 A1 Apr. 25, 2024
US 2024/0230974 A9 Jul. 11, 2024

(30) Foreign Application Priority Data

Jun. 15, 2021 (KR) .................. 10-2021-0077266

(51) Int. Cl.
A61N 5/06 (2006.01)
A61N 5/067 (2006.01)
F21V 8/00 (2006.01)

(52) U.S. Cl.
CPC ......... *G02B 6/0008* (2013.01); *A61N 5/0603* (2013.01); *A61N 5/067* (2021.08); *A61N 2005/0609* (2013.01); *A61N 2005/063* (2013.01)

(58) Field of Classification Search
CPC .................. A61N 5/068; A61N 5/0603; A61N 2005/0609; A61N 2005/063;
(Continued)

(56) References Cited

U.S. PATENT DOCUMENTS 5,415,655 A * 5/1995 Fuller .................... A61B 18/22
606/17
5,557,099 A * 9/1996 Zielinski ................ G01H 1/006
73/660

(Continued)

FOREIGN PATENT DOCUMENTS

KR 10-1999-0013842 A 2/1999
KR 10-0906287 B1 7/2009
(Continued)

OTHER PUBLICATIONS

International Search Report from corresponding PCT Application No. PCT/KR2022/004050, dated Jun. 24, 2022.
(Continued)

Primary Examiner — Eric D. Bertram
(74) Attorney, Agent, or Firm — Harness, Dickey & Pierce, P.L.C.

(57) ABSTRACT

The present disclosure relates to an optical transfer device for tissue treatment. An optical transfer device of the present disclosure includes an optical probe having a light divergence part at the longitudinal end thereof, and a coating part configured to surround the optical probe, wherein the coating part includes a light diffusion part formed at the end
(Continued)

thereof configured to cover the light divergence part, the light diffusion part having multiple grooves formed thereon.

13 Claims, 7 Drawing Sheets

(58) Field of Classification Search
CPC .............. G02B 6/0008; G02B 6/0016; G02B 6/0001–0025; G02B 6/0038–0043; G02B 6/0051
See application file for complete search history.

(56) References Cited

U.S. PATENT DOCUMENTS

| | | | | |
|---|---|---|---|---|
| 2005/0189545 | A1* | 9/2005 | Tazawa | F21S 43/237 257/79 |
| 2005/0254053 | A1* | 11/2005 | Wright | G01N 15/1456 356/432 |
| 2007/0219600 | A1* | 9/2007 | Gertner | A61N 5/0603 607/88 |
| 2007/0239232 | A1* | 10/2007 | Kurtz | G02B 6/001 607/87 |
| 2008/0080206 | A1* | 4/2008 | Charles | A61B 90/36 362/572 |
| 2013/0035746 | A1* | 2/2013 | Bouboulis | A61N 5/0603 607/92 |
| 2017/0203132 | A1* | 7/2017 | Luttrull | A61B 18/1492 |
| 2019/0235161 | A1* | 8/2019 | Ouh | G02B 6/02333 |
| 2020/0054891 | A1* | 2/2020 | Park | A61N 5/0603 |

FOREIGN PATENT DOCUMENTS

| | | |
|---|---|---|
| KR | 10-2010-0013650 A | 2/2010 |
| KR | 10-2011-0091295 A | 8/2011 |
| KR | 10-1610203 B1 | 4/2016 |
| KR | 10-1688827 B1 | 12/2016 |
| KR | 10-2017-0095712 A | 8/2017 |
| KR | 10-1816599 B1 | 1/2018 |
| KR | 10-2020-0019545 A | 2/2020 |

OTHER PUBLICATIONS

Written Opinion of the International Searching Authority from corresponding PCT Application No. PCT/KR2022/004050, dated Jun. 24, 2022.

* cited by examiner

LINEAR PATTERN

OPTICAL PROBE

LIGHT EMITTED FROM LIGHT DIVERGENCE PART

LIGHT EMITTED FROM LIGHT DIVERGENCE PART

OPTICAL TRANSFER DEVICE FOR TISSUE TREATMENT

CROSS-REFERENCE TO RELATED APPLICATIONS

This application is a national phase application of PCT Application No. PCT/KR2022/004050, filed on 23 Mar. 2022, which claims the benefit and priority to Korean Patent Application No. 10-2021-0077266, filed on 15 Jun. 2021. The entire disclosures of the applications identified in this paragraph are incorporated herein by references.

TECHNICAL FIELD

The present disclosure relates to an optical transfer device for tissue treatment and, more particularly, to an optical transfer device for improving optical diffusion of lasers, near-ultraviolet rays, visible rays, near-infrared rays, or the like emitted from an optical fiber probe to a lumen or tubular tissue.

BACKGROUND ART

In order to treat cancer or other symptomatic diseases in a human digestive system (for example, esophagus, stomach, or large intestine), a conventional light transfer device for tissue treatment straightly emits energy (for example, high-output laser) to tissues, and there is a risk that a lumen or tubular tissue will be punctured, peripheral tissues will be thermally damaged, or bleeding or photosensitive sequela will occur.

For example, when attempting an optical treatment (low-output treatment, photodynamic treatment, photothermal treatment, or the like) in connection with a lesion of a lumen or tubular tissue, a conventional light transfer device for tissue treatment transfers light laterally by using an optical fiber probe in some cases, but there is a problem in that the refractive index of the optical fiber and the structural form of the optical fiber surface make it difficult to laterally release light evenly. In addition, the conventional light transfer device for tissue treatment has a problem in that a fixed amount of energy from the end of the optical fiber is also transferred toward the front surface of the end of the optical fiber probe due to the refractive index of the optical fiber and the geometric structure of the optical fiber surface, and there is a possibility that light will be transferred to an undesired tissue area during an optical treatment, thereby burning or damaging the tissue.

Furthermore, when the optical fiber probe of the conventional light transfer device for tissue treatment transfers light to increase the temperature of the lesion during an optical treatment, direct contact between the coating agent surface that protects the optical fiber probe and the lesion tissue may overheat the inside of the optical fiber probe during light emission, thereby degrading the performance of the optical fiber probe or thermally damaging the optical fiber probe and the external protective coating agent.

Therefore, there is a need to solve the degraded efficiency of the optical treatment caused by uneven temperature of the lesion tissue due to uneven diffusion or transfer of light from the optical fiber probe.

As relevant prior art documents, Korean Patent Application Nos. 10-2014-0117908 (Sep. 4, 2014), 10-2007-0084404 (Aug. 22, 2007), and the like may be referred to.

SUMMARY

Technical Problem

Therefore, the present disclosure has been made to solve the above-mentioned problems, and it is an aspect of the present disclosure to provide an optical transfer device wherein, when light such as lasers, near-ultraviolet rays, visible rays, or near-infrared rays is emitted to a target lumen or tubular lesion tissue through an optical fiber probe in order to treat cancer or other symptomatic diseases of a digestive system or the like, wide and even light is diffused and transferred to the tissue, and a partial heat-insulating effect is generated at a place of contact between the tissue and the optical transfer device.

Solution to Problem

Firstly, to summarize the characteristics of the present disclosure, an optical transfer device for tissue treatment according to an aspect of the present disclosure may include: an optical probe having a light divergence part at the longitudinal end thereof; and coating part configured to surround the optical probe, wherein the coating part includes a light diffusion part formed at the end of the coating part configured to cover the light divergence part, the light diffusion part having multiple grooves formed thereon.

The optical transfer device may further include a second coating part configured to surround the coating part.

The multiple grooves are formed on the outer surface of the coating part. However, the multiple grooves may be formed on the inner surface of the coating part when the refractive index of an external medium is smaller than the refractive index of the clad part.

In addition, multiple grooves may be formed on the second coating part from the position of the light divergence part to the end in the longitudinal direction thereof, the multiple grooves of the second coating part may be formed on the outer surface of the second coating part, and the multiple grooves of the second coating part may be formed on the inner surface of the second coating part when the refractive index of an external medium is smaller than the refractive index of the clad part.

The optical probe may include multiple optical elements such as an LED and a laser element, which are provided on the end of a flexible wire or tube, as the light divergence part.

The optical probe may include a second light diffusion part having multiple second grooves formed on the end of an optical fiber wire, as the light divergence part.

It may be preferable that the refractive index of the coating part may be greater than the refractive index of a core of the optical fiber wire.

The second multiple grooves may be formed by mechanically processing a core portion in which a clad is removed from the end of the optical fiber wire.

A core portion, in which a clad is removed from the end thereof, may include a tapered shape, and may be a shape including a ball shape which is additionally formed at the end of a tapered shape and has a large diameter.

A core portion, in which the clad is removed from the end thereof, may include a cylindrical shape, and may include a ball shape which is additionally formed at the end of a cylindrical shape and has a large diameter.

Advantageous Effects of Invention

According to an optical transfer device for tissue treatment according to the present disclosure, the surface structure of a coating agent that protects the end of an optical fiber probe is changed, or a dual-structure coating agent is applied such that when light such as lasers, near-ultraviolet rays, visible rays, or near-infrared rays is emitted to a lumen or tubular lesion tissue, wide and even light may be diffused and transferred to the tissue, and a partial heat-insulating effect may be obtained at a place of contact between the tissue and the optical transfer device.

That is, according to an optical transfer device for tissue treatment according to the present disclosure, transfer of wide and even light to a side surface of the optical transfer device can be induced, transfer of even light to the side surface makes it possible to predict/induce a constant optical reaction inside the tissue, and forward light transfer towards the end of the optical fiber probe can be minimized. In addition, an optical transfer scheme can be adopted selectively and variously according to coating agent surface structure deformation.

In addition, according to an optical transfer device for tissue treatment according to the present disclosure, overheating and damage inside the optical fiber probe occurring during tissue treatment may be prevented, damage to peripheral tissues may be minimized by minimizing transfer of light to the front surface of the optical fiber probe, and a partial heat-insulating effect at a place of contact between the coating agent surface and the lesion tissue during thermotherapy/photothermal treatment of the tissue may induce an efficient optical action or tissue temperature increase.

BRIEF DESCRIPTION OF THE DRAWINGS

The accompanying drawings, which are included as a part of the detailed description to help understanding of the present disclosure, may be used for providing an embodiment of the present disclosure and for describing the technical idea of the present disclosure along with the detailed description.

DETAILED DESCRIPTION

Figure 1:
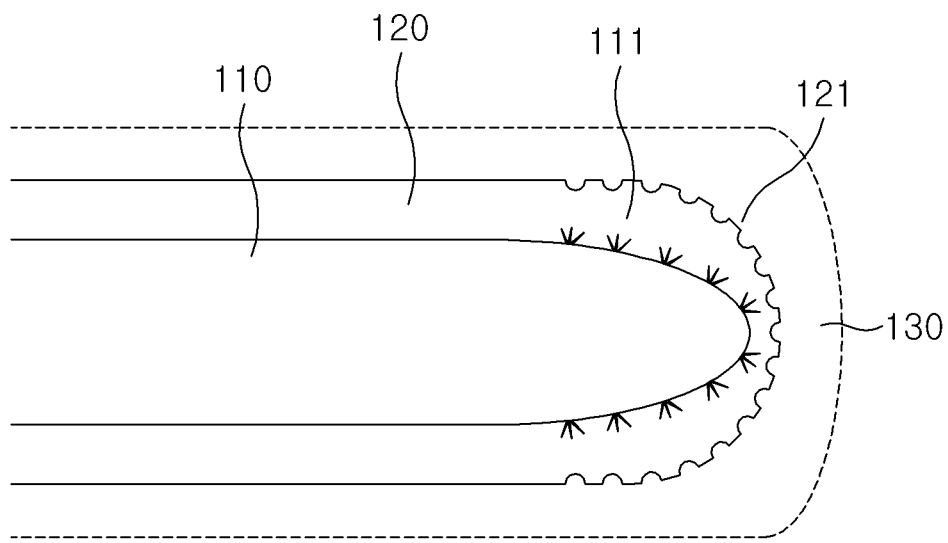
FIG. 1 is a view showing the concept of an optical transfer device according to an embodiment of the present disclosure.

Hereinafter, the present disclosure will be described in detail with reference to the accompanying drawings. In this case, the same elements in each drawing are represented by the same reference numerals as much as possible. In addition, detailed descriptions of already known functions and/or configurations are omitted. In connection with the contents disclosed below, parts necessary for understanding operations according to various embodiments will be mainly described, and descriptions of elements, which may obscure the gist of the description, are omitted. In addition, some elements of the drawings may be exaggerated, omitted, or schematically illustrated. The size of each element does not entirely reflect the actual size thereof, and thus the contents described herein are not limited by the relative size or spacing of the elements drawn in each of the drawings.

In describing the embodiments of the present disclosure, a detailed description of a well-known technology associated with the present disclosure will be omitted when it is considered that the detailed description may unnecessarily make the gist of the present disclosure unclear. In addition, terms to be described below, which are terms defined in consideration of functions thereof in the present disclosure, may vary depending on the intention of a user or an operator, or precedents. Therefore, the terms need to be defined based on contents throughout the present specification. Terms used in a detailed description are merely to just describe the embodiments of the present disclosure, and should not be restrictive in any way. Unless specifically used otherwise, expression of a singular form includes a meaning of a plural form. In the present description, an expression such as "including" or "provided" is intended to indicate certain features, numbers, steps, operations, elements, some or combinations thereof, and should not be construed to preclude the presence or possibility of one or more other features, numbers, steps, operations, elements, some or combinations thereof in addition to the described things.

In addition, terms including as first, second, and the like are used for describing various elements, but the elements are not limited by the terms. In addition, the terms are used only for distinguishing one element from other elements.

First, the principle of disease treatment, which is the purpose of the optical transfer device of the present disclosure and in which light such as a laser rays, near-ultraviolet rays, visible light rays, near-infrared rays, or the like is emitted onto a lumen or tubular lesion tissue to induce stimulation, destruction, incision, or coagulation of cancer of the digestive system or lesion tissue having another symptom, will be described.

<The Principle of Light Therapy>

In connection with the principle of low-power light therapy, generally, light in the wavelength range of 400 to 1000 nm is emitted with an intensity within 100 J/cm$^2$, to activate cells and promote a living body without tissue damage by using a non-invasive or non-thermal method. In low-power light therapy, electromagnetic energy having a predetermined level is emitted to stimulate or inhibit functions of cells, thereby obtaining clinical effects. It may be possible to relief pain, inflammation, or edema, to recover tissue, and to prevent tissue necrosis, by using a light source of near-ultraviolet rays, visible light rays, or near-infrared rays. By low-power optical therapy, the therapeutic effect can be maximized by accurately controlling the wavelengths required for therapy, and appropriately controlling power, the distribution of electromagnetic energy, and the amount of electromagnetic energy. In addition, LED chips may be used in order to generate electromagnetic energy, the power by LED chips differs depending on the wavelength. For example, in the near ultraviolet area of the band of 400 nm, the power of light is 20 mW, and in the band of 850-900 nm band, the power of light is 10 mW or more. In the case of the band of 600-700 nm having effects in healing of damage and relief of pain, an LED chip, which can output the average power of 40 mW, has been developed.

In connection with initial response according to light irradiation, the increase of adenosine triphosphate (ATP) and calcium ions is representative. The energy, which is generated by the increase of ATP and calcium ions, may increase mitochondria potential, may activate a second messenger (cAMP, CGMP, and heat shock protein), and may adjust the amount of reactive oxygen species (ROS). Moreover, due to the adjustment of ROS, it may be possible to induce differentiation, movement, and proliferation of normal cells. In addition, in a damage state thereof, it may be possible to induce antioxidant effect and inflammation relief effect by reducing the amount of ROS.

The mechanism of a low power laser related to a cell function depends on photon absorption by cytochrome c (CCO), and the absorption plays an important role in the production of oxygen metabolism and adenosine 3 phosphoric acid (ATP). The low power laser may increase the concentration of cytochrome C and thus may induce a metabolism effect of longer time, and as a result, there is an effect of improving cell oxygen metabolism. The low power laser may control a molecular dependent biological process such as growth factor production, cell proliferation and movement, and cell death. Fiber blast cell, which is the main mechanism of fibrosis, is metastasized to the myofibroblast by growth factors in the healing process of damage. In this process, the extracellular substrate is abnormally expressed by the excessive expression of the growth factor, so that collagen is formed to cause fibrosis. Red-light of 600 to 800 nm wavelength band may cause an effect of reducing stricture, that is, the expression of inducing growth factors inducing fibrous diseases. The blue-light of the 400 nm wavelength band may function as the direct generation of active oxygen (ROS) and optical stimulation to flavin attached to the composite of the mitochondrial electron transport chain, and may induce and adjust changes of cytokine, growth factors, and inflammatory mediators, which promote inflammation response.

Growth factors may be adjusted by the irradiation of red-light laser. Therefore, Excessive fibrosis activity in metastasis-induction fiber blast cell can be normal. In addition, anti-inflammatory effects may be caused by controlling prostaglandin E2 production and cyclooxygenase (COX) m-RNA expression. In addition, the laser of 600 to 800 nm wavelength band may reduce inflammatory responses, based on the action of peroxide removal enzymes, and the mechanism of active oxygen suppression in blood pressure through catalase activity and movement change of calcium (Ca2). The blue-light laser of the 400 nm wavelength band may function as the direct generation of active oxygen (ROS) and optical stimulation to flavin attached to the composite of the mitochondrial electron transport chain, and may induce and adjust changes of cytokine, growth factors, and inflammatory mediators, which promote inflammation response. The infrared lasers of the 900 nm wavelength band may have anti-inflammatory effects mitigating inflammatory responses, based on the mechanism of reducing immune response to allergic antigens by inhibiting histamine emissions. In addition, infrared lasers may have an effects of cell proliferation, new vascular formation, collagen accumulation, and re-epithelium in the process of healing of damage, based on high transmittance.

Most therapy by low power light is currently applied to the external skin only, and thus therapy using an optical fiber is required in order to treat internal tubular or lumen tissue. The present disclosure provides a method of uniformly transferring light to the side surface of an optical fiber when the optical fiber is used, in the case of photodynamic therapy and light heat therapy as well as low power therapy.

In the case of photodynamic therapy, a photosensitive agent (or photosensitizer) is injected and accumulated into the human body, and light energy is used to destroy diseases or tumors. When the photosensitive agent absorbs light energy, active oxygen (reactive singlet oxygen) is generated to directly cause necrosis or death of cells, thereby removing diseases or tumors. The wavelength band of 600-800 nm is often used in photodynamic therapy, and light energy is emitted after several days after a photosensitive agent is injected. The effect in photodynamic therapy may be different depending on the kind and capacity of a photosensitive agent, the time between drug and light, the wavelength (mW), the intensity of irradiation, the irradiation energy (J), and the number of irradiations thereof. Photodynamic therapy is a photochemical process which does not generate heat and has little effect on connective tissue. Therefore, there is less deformation of underlying tissue compared to therapy using heat. However, in order to significantly affect the therapeutic effect, light should be uniformly transferred to the side surface of an optical fiber.

Differently from low-power laser therapy or photodynamic therapy, photothermal therapy is a therapy method using high energy, in which light energy is transferred to tissue, the chromophore of the tissue absorbs the light, and thus disease or tumor tissue is necrotized by generated high temperature. In the case of photothermal therapy, tissue first absorbs light energy, heat is generated to rise the temperature thereof, and then heat is conducted to the surrounding tissues so as to affect a configuration or bonding of tissues. Various biological changes occur depending on the temperature generated in tissues. For example, when the temperature is 42° C., the thermal effect and protein contraction may occur, when the temperature is 50° C., the enzyme activity may decrease and cell movement may slow down, when the temperature is 60-70° C., protein denaturation and coagulation may occur, when the temperature is 80° C., an osmotic membrane phenomenon of the cell membrane may occur, when the temperature is 100° C., vaporization, pyrolysis, removal, and destruction may occur, and when the temperature is 100° C. or more, dissolution, carbonization, and the like may occur. In order to induce tissue changes according to temperature rise, light energy should be uniformly transferred, and thus high therapeutic effect and safety may be secured. The temperature rise ($\Delta T$, ° C.) may be predicted using the following [Equation 1]. Here, $\mu_a$ is the tissue absorption rate (1/cm), H is the light energy per unit area (J/cm$^2$), $\rho$ is the tissue density (kg/cm$^3$), and c is the tissue specific heat (J/kgK). In order to enhance photothermal therapy effect, the temperature should be selected in consideration of light energy, pulse length, beam size, repetition rate, wavelength, and optical/thermal properties of the tissue.

$$\Delta T = \mu_a H/\rho c \qquad \text{[Equation 1]}$$

Hereinafter, an optical transfer device of the present disclosure will be described in detail, for low power therapy, photodynamic therapy, photothermal therapy, or the like. According to the optical transfer device, through an optical fiber probe and the side surface of an optical fiber, light such as a laser rays, near-ultraviolet rays, visible light rays, near-infrared rays may be widely and uniformly diffused and transferred to tissues, and partial heat-insulating effects may occur in a portion with which tissues and the optical transfer device come into contact.

FIG. 1 is a view showing the concept of an optical transfer device 100 according to an embodiment of the present disclosure.

Referring to FIG. 1, the optical transfer device 100 for tissue treatment according to an embodiment of the present disclosure may include an optical probe 110 and a coating part 120, and may further include a second coating part 130 configured to surround the coating part 120 as necessary. The second coating part 130 may be added for a function of additional diffusion of light, insulation, or protection from foreign materials, and may enable a double-clad structure together with the coating part 120 to be formed.

The optical transfer device 100 may be made of a thin and long flexible material, which enables the optical transfer device 100 to be directly inserted into or removed from the lumen or tubular lesion tissue of the human body, or enables the optical transfer device 100 to be inserted into or removed from another tube inserted into the lumen or tubular lesion tissue of the human body.

The end of the optical probe 110 may be a portion from which necessary light such as laser rays, near-ultraviolet rays, visible light rays, near-infrared rays is emitted, and light provided from a light source (not shown) is diverged and diffused through a light divergence part 111 of the longitudinal end of the optical probe 110.

The coating part 120 may be a portion configured to surround the optical probe 110, and the coating part 120 may include a light diffusion part 121, which is formed at the end of the coating part 120, which is configured to cover the light divergence part 111 and has multiple grooves formed thereon. The drawings illustrate the second coating part 130 on which grooves are not formed. However, grooves may not be formed on the second coating part 130, and if necessary, multiple grooves, which have the same shapes as the grooves of the light diffusion part 121, may be formed from the position of the light divergence part 111 to the end in the longitudinal direction thereof. The role and function of the grooves of the light diffusion part 121 of the first coating part 120 may be applied, as it is, to the grooves formed on the second coating part 130. As described below, multiple grooves of the second coating part 130 may also be formed on the outer surface thereon. In addition, when the refractive index of an external medium is smaller than the refractive index of the second coating part 130, the corresponding grooves of the second coating part 130 may also be formed on the inner surface of the second coating part 130.

Figure 2:
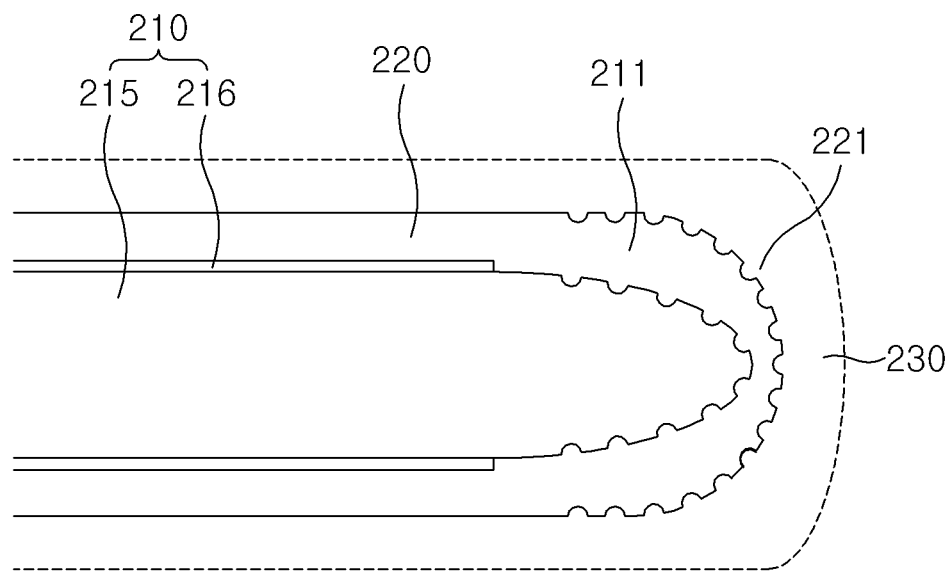
FIG. 2 is a view showing an optical transfer device according to another embodiment of the present disclosure.

FIG. 2 is a view showing an optical transfer device 200 according to another embodiment of the present disclosure.

Referring to FIG. 2, the optical transfer device 100 for tissue treatment according to another embodiment of the present disclosure may include the optical probe 210 and a coating part 220, and may further include a second coating part 230 configured to surround the coating part 220 as necessary. The second coating part 230 may be added for a function of additional diffusion of light, insulation, or protection from foreign materials, and may enable a double clad-structure together with the coating part 220 to be formed.

The optical transfer device 200 may also be made of a thin and long flexible material, which enables the optical transfer device 200 to be directly inserted into or removed from the lumen or tubular lesion tissue of the human body, or enables the optical transfer device 200 to be inserted into or removed from another tube inserted into the lumen or tubular lesion tissue of the human body.

The end of the optical probe 210 may be a portion from which necessary light such as laser rays, near-ultraviolet rays, visible light rays, near-infrared rays is emitted, and light provided from a light source (not shown) is diverged and diffused through a light divergence part 211 of the longitudinal end of the optical probe 210. Here, the optical probe 210 may be formed of an optical fiber wire including a core 215 and a clad 216, and may include a light diffusion part 211 which has multiple grooves formed on the longitudinal end thereof, as a light divergence part 211. Light provided from a light source of an external optical device such as light-emitting diodes (LEDs) or laser generating devices (e.g., an optical device such as light semiconductor laser diodes, pulsed lasers, or diode pumped solid state (DPSS) lasers or lamp pumped (LP) lasers for continuous wave lasers), may be transferred through the optical fiber wire and may be diffused through the multiple grooves of the light diffusion part 211. In order for effective diffusion from the light diffusion part 211, the refractive index of the coating part 220 may be greater than or equal to the refractive index of the light diffusion part 211. In addition, the refractive index of the second coating part 230 may be greater than or equal to the refractive index of the coating part 220. The refractive index of the core 215 may be greater than the refractive index of the clad 216, the multiple grooves of the light diffusion part 211 may be formed on a portion corresponding to the core portion in which the clad is removed from the end of the optical fiber wire, and the grooves may be formed by a mechanically processing (e.g., grinding, polishing, laser processing, or etc.) the core portion from which the clad is removed. In some cases, in addition to the above mechanical processing, methods such as chemical etching may be used.

Figure 3:
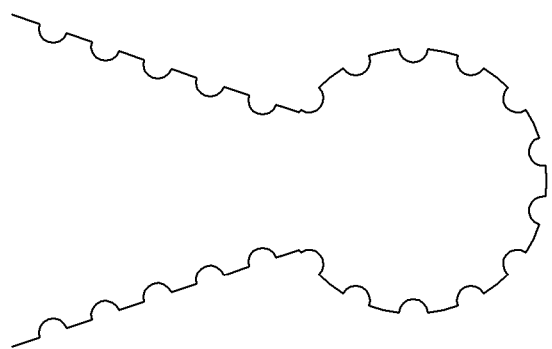
FIG. 3 is a view illustrating an example of a shape including a ball shape which is additionally formed at the end of a tapered shape end and has a large diameter, as a shape of a light diffusion part of an optical probe of FIG. 2.
Figure 4:
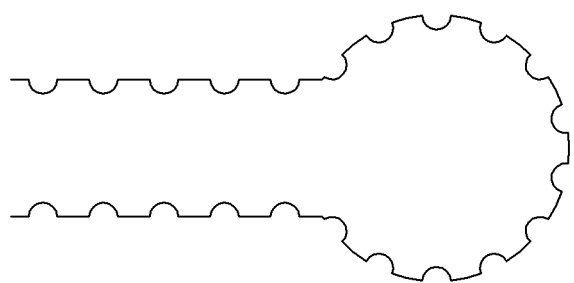
FIG. 4 is a view illustrating an example of a shape including a ball shape which is additionally formed at the end of a cylindrical shape and has a large diameter, as a shape of a light diffusion part of an optical probe of FIG. 2.

As illustrated in the drawings, the shape of the core portion, in which the clad is removed from the end of the optical fiber wire, may be a tapered shape (or conical shape) which has a diameter decreasing as going toward the end thereof. In addition, the shape thereof may be a cylindrical shape having a predetermined diameter (however, it may be possible that the end thereof has a round shape). As illustrated in FIG. 3, the shape of the core portion, in which the clad is removed from the end of the optical fiber wire, may be a shape including a ball shape which is additionally formed at the end of the tapered shape and has a large diameter. In addition, as illustrated in FIG. 4, the shape of the core portion in which the clad is removed from the end of the optical fiber wire, may be a shape including a ball shape which is additionally formed at the end of the cylindrical shape and has a large diameter. The grooves of the light diffusion part 211 may be configured to allow light to be uniformly diffused in the side surface thereof and the end of the longitudinal end extending therefrom, and particularly, may be configured to minimize that light is directed toward the front of the longitudinal end side of the optical probe 210, and to allow most of light energy to be uniformly transferred to the side surface thereof. By applying the combined shape illustrated in FIG. 3 and FIG. 4, the grooves of the light diffusion part 211 may enables light directed toward the front of the longitudinal end side of the optical probe 210 to be minimized, and may enable most of light energy to be uniformly transferred to the side surface thereof.

The coating part 220 may be a portion configured to surround the optical probe 210, and the coating part 220 may include a light diffusion part 221, which is formed at the end of the coating part 120, which is configured to cover the light divergence part 211 and has multiple grooves formed thereon. The drawings illustrate the second coating part 230 on which grooves are not formed. However, grooves may not be formed on the second coating part 230, and if necessary, multiple grooves, which have the same shapes as the grooves of the light diffusion part 221, may be formed from the position of the light divergence part/light diffusion part 211 to the end in the longitudinal direction thereof. The role and function of the grooves of the light diffusion part 221 of the first coating part 220 may be applied, as it is, to the grooves formed on the second coating part 230. As described below, multiple grooves of the second coating part 230 may also be formed on the outer surface thereon. In addition, when the refractive index of an external medium is smaller than the refractive index of the second coating part 230, the corresponding grooves of the second coating part 230 may also be formed on the inner surface of the second coating part 230.

Figure 5:
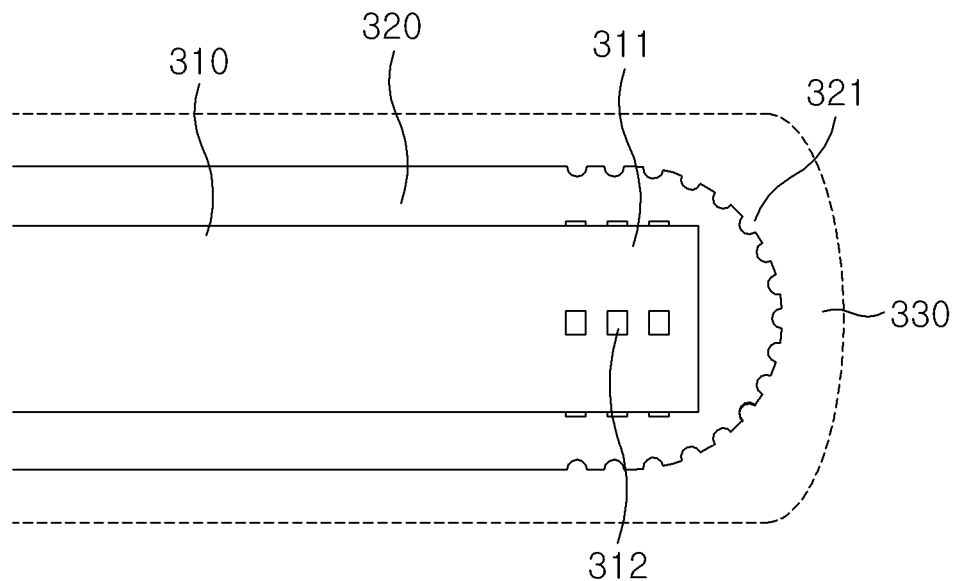
FIG. 5 is a view showing an optical transfer device according to another embodiment of the present disclosure.

FIG. 5 is a view showing an optical transfer device 300 according to another embodiment of the present disclosure.

Referring to FIG. 5, the optical transfer device 300 for tissue treatment according to another embodiment of the present disclosure may include the optical probe 310 and a coating part 320, and may further include a second coating part 330 configured to surround the coating part 320 as necessary. The second coating part 330 may be added for a function of additional diffusion of light, insulation, or protection from foreign materials, and may enable a double-clad structure together with the coating part 320 to be formed.

The optical transfer device 300 may also be made of a thin and long flexible material, which enables the optical transfer device 300 to be directly inserted into or removed from the lumen or tubular lesion tissue of the human body, or enables the optical transfer device 200 to be inserted into or removed from another tube inserted into the lumen or tubular lesion tissue of the human body.

The end of the optical probe 310 may be a portion from which necessary light such as laser rays, near-ultraviolet rays, visible light rays, near-infrared rays is emitted, and light provided from a light source 312 is diverged and diffused through a light divergence part 311 of the longitudinal end of the optical probe 310. Here, the optical probe 310 may be a flexible wire or tube and may include multiple optical devices 312 formed on the end of a flexible wire or tube as a light divergence part 311. The multiple optical devices 312 of the light divergence part 311 may be configured to receive, through a cable, power through the wire or tube so as to generate light. In addition, in some cases, the multiple optical devices 312 of the light divergence part 311 may be configured receive a power source remotely provided through a radio frequency (RF) method. In order to receive a wireless power supply, the light divergence part 311 may include an antenna for receiving a wireless signal and a power part for converting an output of the antenna into a predetermined power voltage. The optical device 312 may be light-emitting diodes (LEDs) or laser generating devices (e.g., an optical device such as light semiconductor laser diodes, pulsed lasers, or diode pumped solid state (DPSS) lasers or lamp pumped (LP) lasers for continuous wave lasers).

The coating part 320 may be a portion configured to surround the optical probe 310, and the coating part 320 may include a light diffusion part 321, which is formed at the end of the coating part 120, which is configured to cover the light divergence part 311 and has multiple grooves formed thereon. The drawings illustrate the second coating part 330 on which grooves are not formed. However, grooves may not be formed on the second coating part 330, and if necessary, multiple grooves, which have the same shapes as the grooves of the light diffusion part 321, may be formed from the position of the light divergence part/optical devices 312 to the end in the longitudinal direction thereof. The role and function of the grooves of the light diffusion part 321 of the first coating part 320 may be applied, as it is, to the grooves formed on the second coating part 330. As described below, multiple grooves of the second coating part 330 may also be formed on the outer surface thereon. In addition, when the refractive index of an external medium is smaller than the refractive index of the second coating part 330, the corresponding grooves of the second coating part 330 may also be formed on the inner surface of the second coating part 330.

In the optical transfer device 100, 200, or 300, the transmission wavelength may be preferably from 400 nm to 3000 nm, and the case of transmission power, it may be preferably that 0.01 W to 100 W can be transmitted.

The coating part 120, 220, or 320 may be made of a coating material having heat resistance, chemical resistance, and biological safety, and may be made of glass (SiO2), quartz, polyether ether ketone (PEEK), ethylene tetra fluoro ethylene (ETFE), per fluoro alkoxy (PFA), poly tetra fluoro ethylene (PTFE), or the like.

The second coating part 130, 230, or 330 may be made of a coating material having heat resistance, chemical resistance, and biological safety, and may be made of the same material as the first coating part 120, 220, or 320. However, the second coating part 130, 230, or 330 may transmit, in whole or in part, light of a wavelength of 400 nm to 3000 nm. In order for functions of additional diffusion of light, insulation, protection from foreign materials, or etc., the second coating part 130, 230, or 330 may be made of polytetrafluoroethylene (PTFE), polyethylene, polyvinyl Chloride, nylon 66, 11, 12, urethanes, polyurethanes, polypropylene, polycarbonate, ABS, Pebax, polyetheretherketone (PEEK), polyethylene terephthalate (PET), and the like.

Figure 6:
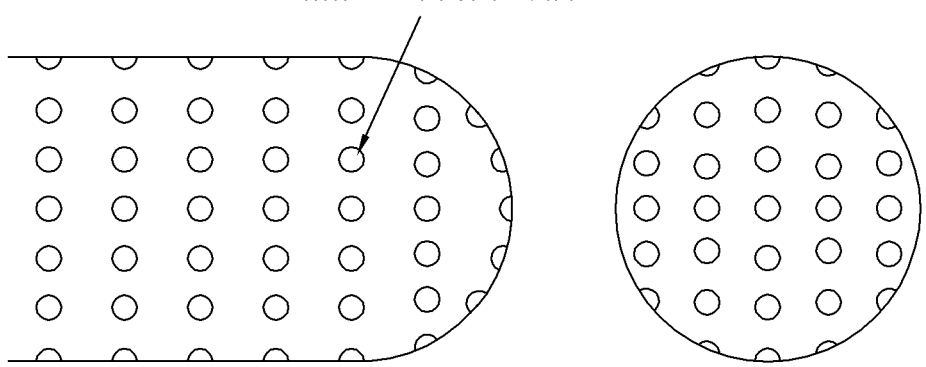
FIG. 6 is a view illustrating an example of grooves formed on a light diffusion part, in the embodiments of the present disclosure.

FIG. 6 is a view illustrating an example of grooves formed on a light diffusion parts 211, 121, 221, and 321, in the embodiments of the present disclosure.

Figure 7:
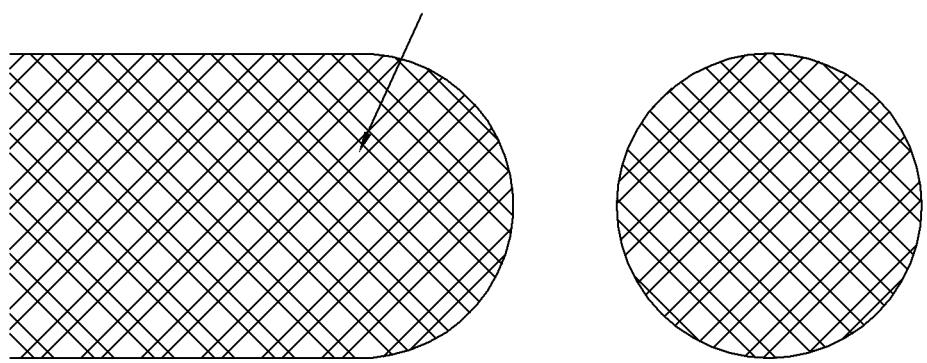
FIG. 7 is a view illustrating another example of grooves formed on a light diffusion part, in the embodiments of the present disclosure.

FIG. 7 is a view illustrating another example of grooves formed on a light diffusion parts 211, 121, 221, and 321, in the embodiments of the present disclosure.

Figure 8A:
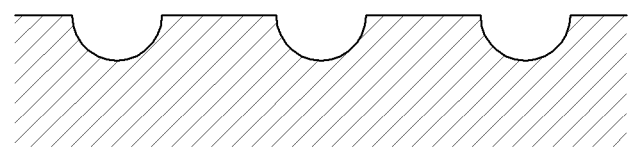
FIGS. 8A, 8B and 8C are views illustrating various shapes of grooves formed on a light diffusion part, in the embodiments of the present disclosure.
Figure 8B:
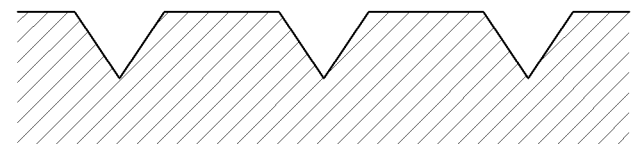
Figure 8C:
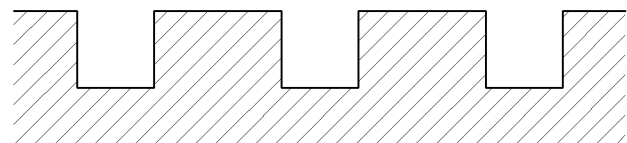

In FIG. 6 and FIG. 7, the figures on the left are side views, and the figures on the right are front views seen from the end thereof. The grooves, which is illustrated FIG. 6 and FIG. 7, of the light diffusion parts 211, 121, 221, and 321, that is, the grooves of the light diffusion part 211 (FIG. 2) of the optical probe 210 and the light diffusion part 121, 221, and 321 (FIGS. 1, 2, and 5) of the coating part 120, 220, and 320, may be formed on the outer surface thereof in a curve shape as illustrated in FIG. 8A, in a V-shape as illustrated in FIG. 8B, in a rectangle shape as illustrated in FIG. 8C, in a polygonal shape, or the like.

In some cases, the grooves of the light diffusion parts 211, 121, 221, and 321 may be formed in a shape in which a dimple shape or a linear shape is irregularly combined. However, as illustrated in FIGS. 6 and 7, in order to uniformly diffuse light from the side surfaces of the diffusion parts 211, 121, 221, and 321 to the ends of the longitudinal ends extending therefrom, it may be preferable that the diffusion parts 211, 121, 221, and 321 have grooves uniformly (it may be selectively possible in a part or the whole thereof) formed along the corresponding surfaces thereof. The dimple-shaped grooves may include a curve-shaped groove, a V-shaped groove, a polygonal-shaped groove, or the like, in a two-dimensional array shape having predetermined intervals. In addition, the linear-shaped grooves may include linear grooves parallel to one direction (grooves which have a predetermined width and are continuously formed), and linear grooves parallel to different directions. The pattern of the grooves of the diffusion parts 211, 121, 221, and 321 may be formed to have diameters or widths of several μm to several hundreds μm (e.g., 5 to 500 μm) according to design.

The grooves of the light diffusion parts 211, 121, 221, and 321 may be configured to allow light to be uniformly diffused in the side surface thereof and the end of the longitudinal end extending therefrom, and particularly, may be configured to minimize that light is directed toward the front of the longitudinal end side of the optical probes 110, 210, and 310 and to allow most of light energy to be uniformly transferred to the side surface thereof.

In addition, when light is emitted into tissue, air is introduced into the dimple-shaped grooves or linear-shaped grooves of the light diffusion parts 211, 121, 221, 321, and is trapped in the space of the grooves. The trapped air layer may induce partial heat-insulating effects such that heat generated from the surface of tissue is not transferred inside the first coating part 120, 220, or 320, the second coating part 130, 230, or 330, or the optical probe 110, 210, or 330. Therefore, when light is emitted into tissue, although the surface temperature of the tissue rises, the trapped air layers may prevent or minimize a phenomenon that some tissues are attached to the first coating part 120, 220, or 320, and the second coating part 130, 230, and 330.

Figure 9:
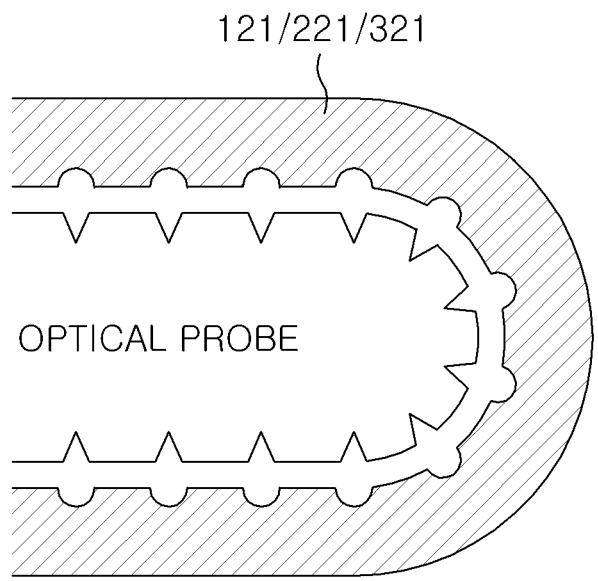
FIG. 9 is a view illustrating shapes of grooves formed inside light diffusion parts of coating parts, in the embodiments of the present disclosure.

FIG. 9 is a view illustrating shapes of grooves formed inside light diffusion parts 121, 221, and 321 of coating parts 120, 220, and 320, in the embodiments of the present disclosure.

Referring to FIG. 9, the grooves (a curved shape, V-shape, polygonal shape, or the like), which are formed on the light diffusion parts 121, 221, and 321 of the coating part 120, and 220, and 320, may be formed on the inner surface of the inner surface on the coating part 120, 220, and 320 also. It may possible that light is easily diffused to the outside even when the refractive index of an external medium of the coating part 120, 220, or 320 is smaller than the refractive index of the coating part 120, 220, or 320.

Figure 10:
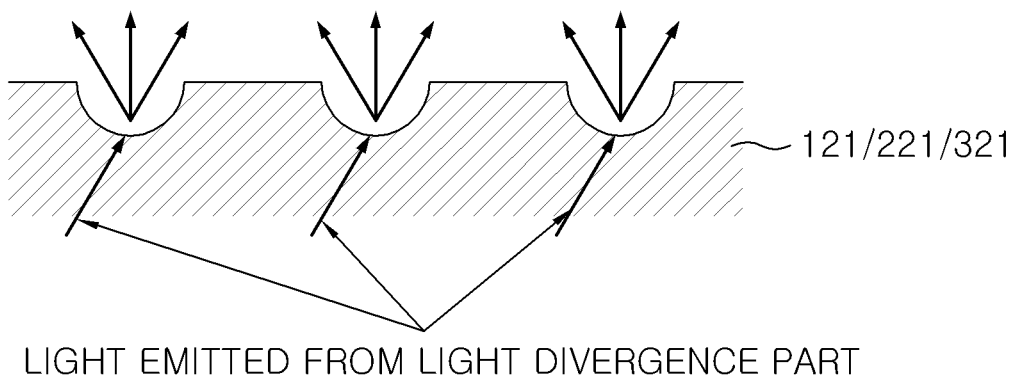
FIG. 10 is a view showing diffusion of light by side grooves formed on light diffusion parts of coating parts, in the embodiments of the present disclosure.

FIG. 10 is a view showing diffusion of light by side grooves formed on a light diffusion part 121, 221, or 321 of a coating part 120, 220, or 320, in the embodiments of the present disclosure.

Referring to FIG. 10, the conventional optical probe does not have a groove pattern for light diffusion, as the light diffusion parts 121, 221, and 321 of the present disclosure. Therefore, in the case of the conventional optical fiber probe, light is scattered/diffused only on the surface thereof. Accordingly, a very small amount of light is emitted, and light is non-uniformly emitted with a narrow range. As a result, the side grooves of the light diffusion parts 121, 221, and 321 of the present disclosure may cause large amount of light to be uniformly diffused to the side surface thereof.

According to the embodiments of the present disclosure, light is primarily emitted from the light divergence part 111, 211, or 311 inside the coating part, is scattered or diffused, and then is emitted. In addition, additionally, the grooves formed on the light diffusion parts 121, 221, and 321 of the coating part 120, 220, and 320 allow light to be diffused with a large angle so that light is uniformly emitted over a wide range. The irradiation, scattering, or diffusion of light is preformed over two steps, to further increase the light diffusion effect and to transfer a larger amount of light energy thereto while uniformly distributing light energy to the side direction thereof.

The groove pattern of the grooves formed on the light diffusion parts 121, 221, and 321 of the coating part 120, 220, and 320 may be formed to have a diameter or a width from the size of several μm to the size of several hundreds of μm, and thus a light diffusion range and a transfer light energy in the side direction thereof can be adjusted according to the purpose. In addition, the groove pattern of the light diffusion parts 121, 221, and 321 of the coating part 120, 220, and 320 may be formed periodically, continuously (e.g., linearly continuously), discretely (e.g., linearly non-continuously), partially, or the like, and thus a light diffusion range and light irradiation form in the side direction thereof can be adjusted. A light distribution map in the transverse sectional view of light according to the groove pattern of the light diffusion parts 121, 221, and 321 may be formed in a flat-top distribution, a Gaussian distribution, a left-skewed distribution, a right-skewed distribution, a fractional distribution, a diffuse distribution, a radial distribution, or the like.

Figure 11:
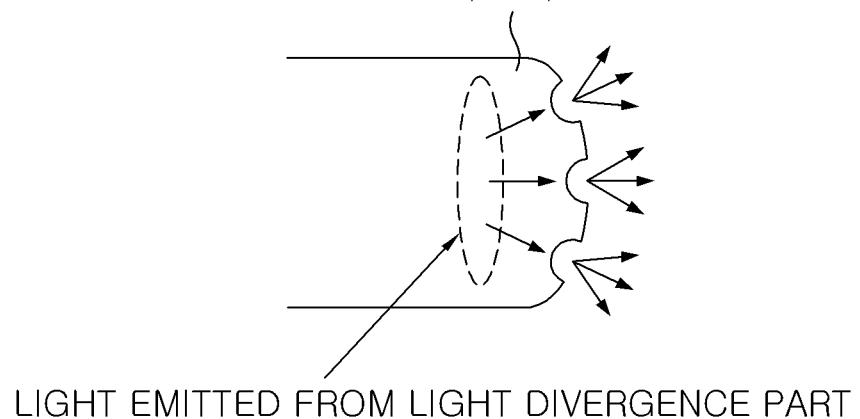
FIG. 11 is a view showing diffusion of light by grooves formed at the end of the longitudinal direction of light diffusion parts of coating parts, in the embodiments of the present disclosure.

FIG. 11 is a view showing diffusion of light by grooves formed at the ends of the longitudinal direction of light diffusion parts 121, 221, and 321 of coating parts 120, 220, and 320, in the embodiments of the present disclosure.

Referring to FIG. 11, the conventional light fiber probe does not have a groove pattern on the longitudinal of the end for light diffusion, as the light diffusion parts 121, 221, and 321 of the present disclosure. Therefore, in the case of the conventional optical fiber probe, light is scattered/diffused only on the surface thereof. Accordingly, a large amount of light is emitted to the front of the longitudinal end of the optical fiber probe. As a result, the grooves of the longitudinal ends of the light diffusion parts 121, 221, and 321 of the present disclosure may minimize that the light from light divergence parts 111, 211, and 321 is transferred to the front thereof. The light emitted from the light divergence parts 111, 211, and 311 to the front, through the longitudinal end grooves of the light diffusion parts 121, 221, and 321 of the present disclosure, may be distributed at various angles, and thus the light may be uniformly and widely diffused to the side surface thereof.

In the embodiments of the present disclosure, light is primarily emitted from the light divergence part 111, 211, or 311 inside the coating part, is scattered or diffused, and then is emitted. In addition, additionally, the grooves formed on the longitudinal ends of the light diffusion parts 121, 221, and 321 of the coating part 120, 220, and 320 cause light to be diffused so that light is uniformly emitted to the side surface thereof over a wide range. The irradiation, scattering, or diffusion of light is preformed over two steps, to further increase the light diffusion effect. In addition, light is transferred to the direction of the longitudinal end so as to prevent the occurrence of the undesired burns and damage of tissue.

The groove pattern of the longitudinal end grooves formed on the light diffusion parts 121, 221, and 321 of the coating part 120, 220, and 320 may be formed to have a diameter or a width from the size of several μm to the size of several hundreds of μm, and thus a light diffusion range and a transfer light energy in the front direction of the longitudinal end can be adjusted according to the purpose. In addition, the groove pattern of the longitudinal end of the light diffusion parts 121, 221, and 321 of the coating part 120, 220, and 320 may be formed periodically, continuously (e.g., linearly continuously), discretely (e.g., linearly non-continuously), partially, or the like, and thus a light diffusion range and light irradiation form in the front direction of the longitudinal end can be adjusted. A light distribution map in the transverse sectional view of light in the front direction of the longitudinal end according to the groove pattern of the light diffusion parts 121, 221, and 321 may be formed in a flat-top distribution, a Gaussian distribution, a left-skewed distribution, a right-skewed distribution, a fractional distribution, a diffuse distribution, a radial distribution, or the like.

Figure 12:
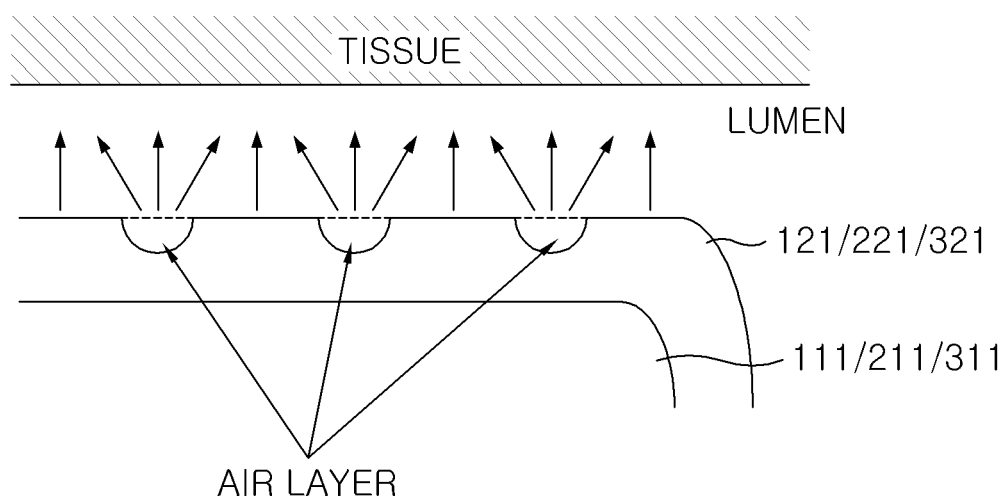
FIG. 12 is a view showing a heat-insulating effect due to grooves formed on light diffusion parts of coating parts, in the embodiments of the present disclosure.

FIG. 12 is a view showing a heat-insulating effect due to grooves formed on light diffusion parts 121, 221, and 321 of coating parts 120, 220, 320, in the embodiments of the present disclosure.

Referring to FIG. 12, when light having high energy is emitted through the optical transfer devices 100, 200, and 300, the temperature rise of tissue may be caused, and heat transfer between tissue and the device may be done. However, in the coating parts 120, 220, and 320 of the present disclosure, a heat-insulating effect may occur through the light diffusion part 121, 221, and 321.

In order for light therapy, when the side of the light diffusion part 121, 221, or 321, which corresponds to the distal end of the longitudinal direction of the optical transfer device 100, 200, 300, comes into contact with tissue, air is partially trapped in the space formed by the groove pattern concavely formed on the surface to form air layer. Due to the change in the surface structure of the coating part 120, 220, or 320, the light emitted from the optical probe 110, 210, or 310 is additionally diffused so that the light is uniformly and widely distributed to the tissue-to-be-treated. When light having high energy is emitted to tissue, heat is generated in the tissue, and thus the temperature thereof rises. Therefore, as the temperature rises, heat of the coating part 120, 220, or 320 is conducted into a clad agent. The thermal conductivity of the sheathing material of the coating part 120, 220, or 320 may be at least 0.2 W/mK. In addition, in the case of Quartz, the thermal conductivity may be as high as 1.5 W/mK, and thus a large amount of heat generated from tissue may be transferred to the clad agent of the coating part 120, 220, or 320, and up to the optical probe 110, 210, 310 of the optical fiber therein. As the amount of the transferred heat increases, depending on the thermal durability of the clad agent of the coating part 120, 220, or 320, and the volume in which the optical probe 110, 210, or 310 is positioned, thermal stress is generated inside the optical transfer device 100, 200, 300, and thus damage or destruction thereof is caused. However, when the structure of the diffusion type coating part 120, 220, or 320) of the present disclosure is used, an air layer is formed on the surface thereof. Therefore, even when the temperature rises due to the heat generated in tissue, the heat is conducted into the coating part 120, 220, or 320, and the air layer trapped on the surface together. Since the thermal conductivity of air is 0.02 W/mK and is more than 10 times lower than the thermal conductivity of the clad agent. Therefore, when heat is conducted from tissue to the clad agent, the air layer may function as an insulating material. By the partial thermal insulation effects due to the trapped air layer, the conduction of heat generated from tissue to the clad agent is minimized. Therefore, the thermal stress generated in the coating part 120, 220, or 320, or the optical probe 110, 210, or 310, can be reduced. In addition, by the partial thermal insulation effects due to the air layer, more heat may be retained on or inside and transferred to the surface of tissue surface, thereby increasing the therapeutic effect.

Figure 13:
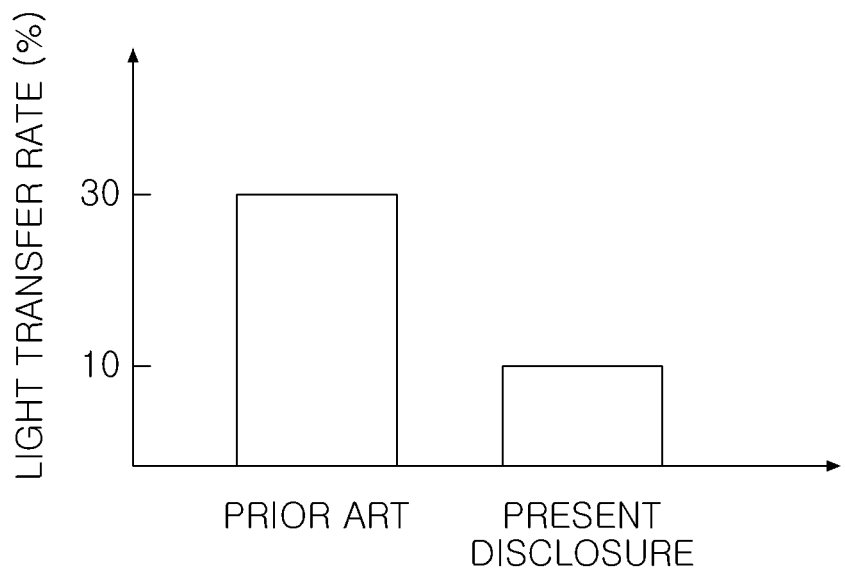
FIG. 13 is a graph showing a comparison of the measured rate of transfer of light to the front of a longitudinal end between a conventional optical transfer scheme and a secondary diffusion-typed optical transfer scheme in connection with an optical transfer device of the present disclosure.

FIG. 13 is a graph showing a comparison of the measured rate of transfer of light to the front of a longitudinal end between a conventional optical transfer scheme and a secondary diffusion-typed optical transfer scheme in connection with an optical transfer device 100, 200, or 300 of the present disclosure.

Referring to FIG. 13, in the case of the conventional general sheath, due to the light energy diffused from the front of the longitudinal end of the optical fiber probe and the like, the light transfer rate, in which light is transferred to the front, is as high as 30%. Due to the high light transfer rate in which light is transferred to the front, at the time of phototherapy of tissue, there may be caused a problem of burns or damage to tissue since undesired light is transferred to tissue.

On the other hand, as the light diffusion part 121, 221, or 321 of the coating part 120, 220, or 320 of the present disclosure, when a secondary diffusion-typed light transfer type clad is used, due to the light diffusion by the groove pattern of the longitudinal end of the coating part 120, 220, or 320 positioned at the end of the optical transfer device 100, 200, or 300, the light energy diverged from the optical probe 110, 210, or 310 to the front is additionally diffused. Due to the additional light diffusion, the light transfer rate, in which light is transferred to the front, is as low as 10% or less. Due to the low light transfer rate in which light is transferred to the front, at the time of phototherapy of tissue, the light is induced such that more light energy is transferred to the side surface, and thus unnecessary burns or damage to tissue can be minimized.

Figure 14:
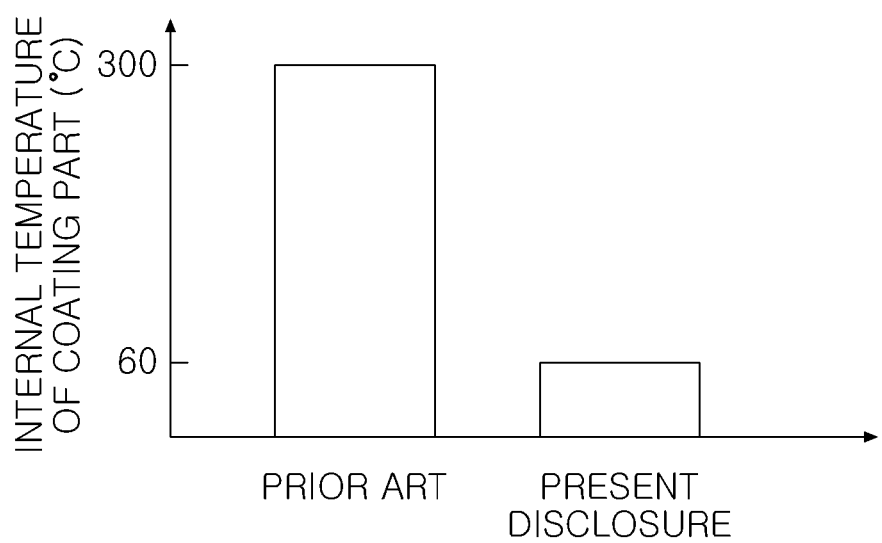
FIG. 14 is a graph showing a comparison of the measured internal temperature of a clad material between a conventional optical transfer scheme and a secondary diffusion-typed optical transfer scheme in connection with an optical transfer device of the present disclosure.

FIG. 14 is a graph showing a comparison of the measured internal temperature of a clad material between a conventional optical transfer scheme and a secondary diffusion-typed optical transfer scheme in connection with an optical transfer device 100, 200, or 300 of the present disclosure.

Referring to FIG. 14, in the case of conventional general sheath, when light is emitted, light diffusion is small at the portion into contact with tissue, and the internal temperature of the clad agent rapidly rises due to the overall thermal insulation effect. The internal temperature thereof is measured up to a maximum temperature of 300° C. depending on the light irradiation time, and depending on the thermal properties of the clad agent, damage to the clad agent or the optical fiber probe may occur.

On the other hand, as the light diffusion part 121, 221, or 321 of the coating part 120, 220, or 320 of the present disclosure, when a secondary diffusion-typed light transfer type clad is used, due to the air layer partially formed by the groove pattern of the longitudinal end the coating part 120, 220, or 320 positioned at the end of the optical transfer device 100, 200, or 300, light diffusion is widely induced in the portion into contact with tissue when light is irradiated, and a partial thermal insulation effect is induced to minimize the increase in the internal temperature of the clad agent. The maximum temperature of the clad agent is determined by the light irradiation time, but under the above conditions, if the internal temperature of the clad agent is lowered to 60° C., it may be possible to prevent thermal deformation of the clad agent or the temperature rise of optical fibers of the light divergence part 111, 211, or 311.

As described above, according to the optical transfer device 100, 200, or 300 for tissue therapy according to the present disclosure, the clad agent for protecting the end of an optical fiber of the light divergence part 111, 211, or 311, that is, a changed surface structure of the first coating part 120, 220, or 320, or a double structure, to which the second coating part 130, 230, or 330 is added, applied thereto. Therefore, when light such as laser rays, near-ultraviolet rays, visible light rays, and near-infrared rays, or the like is emitted to lumen or tubular lesion tissues, light can be widely and uniformly diffused and transferred to tissue, and a partial thermal insulation effect can occur in a portion with which tissues and the optical transfer device come into contact. According to the optical transfer device 100, 200, or 300 for tissue therapy according to the present disclosure, light may be induced such that light is widely and uniformly transferred to the side surface of the end of the optical transfer device 100, 200, or 300. In addition, since light is uniformly transferred to the side surface, it may be possible to predict/induce a light response in tissue. In addition, it may be minimized that light is transferred to the front surface in the end direction of the optical fiber or the like of the light divergence part 111, 211, or 311. In addition, various light transfer methods may be selectively adopted according to the modification of the surface structure of the clad agent.

According to the optical transfer device 100, 200, or 300 for tissue therapy according to the present disclosure, it may be possible to prevent overheating and damage of the optical fiber or the like of the light divergence part 111, 211, or 311, which occurs at the time of tissue therapy, and it may be possible to minimize damage of surrounding tissues by minimizing that light is transferred to the front surface of the optical fiber or the like. In addition, during thermal/photothermal treatment of tissues, due to a partial thermal insulation effect in the contact portion of the surface of the clad agent and lesion tissue, it may possible to induce an efficient light action or the increase of tissue temperature.

Although the present disclosure has been described above with reference to particular contents such as specific elements, the limited embodiments, and the drawings, the above-described embodiments are provided merely for the purpose of helping overall understanding of the present disclosure, and the present disclosure is not limited to the embodiments. In addition, the above-described embodiments may be variously modified and changed altered by a person skilled in the art, which belongs to the technical field of the present disclosure, without departing intrinsic features of the present disclosure. Accordingly, the spirit of the present disclosure should not be limited to the described embodiment, and it should be interpreted that all of the equivalents or equivalent modifications of the claims as well as the appended claims belong to the scope of the spirit of the present disclosure.

What is claimed is:

1. An optical transfer device for tissue treatment, comprising:
   an optical probe of a flexible material having a light divergence part at a longitudinal end of the flexible material;
   a first coating part extending from the position of the flexible material of the optical probe without the light divergence part and entirely surrounding the light divergence part; and
   a second coating part surrounding the first coating part, extending from the position of the flexible material of the optical probe without the light divergence part and entirely surrounding to a longitudinal end of the first coating part,
   wherein the first coating part comprises a light diffusion part formed at an end of the first coating part and configured to cover the light divergence part, the light diffusion part having multiple grooves formed thereon,
   wherein the second coating part includes multiple grooves formed from the position of the light divergence part to the end of the second coating part in a longitudinal direction, and
   wherein the optical transfer device is configured such that the first coating part surrounds the optical probe and the second coating part surrounds the first coating part,
   wherein the optical transfer device is a flexible structure, and
   wherein the optical transfer device is configured to be directly inserted into or removed from a lumen or tubular lesion tissue of a human body, or a tube is configured to be first inserted into a lumen or tubular lesion tissue of a human body and the optical transfer device is configured to be inserted into or removed from the tube.

2. The optical transfer device of claim 1, wherein:
   the multiple grooves of the light diffusion part are formed on an outer surface of the first coating part relative to the light diffusion part.

3. The optical transfer device of claim 1, wherein:
   the multiple grooves are formed on an inner surface of the first coating part relative to the light diffusion part.

4. The optical transfer device of claim 1, wherein:
   the multiple grooves of the second coating part are formed on an outer surface of the second coating part relative to the light diffusion part.

5. The optical transfer device of claim 1, wherein:
   the multiple grooves of the second coating part are formed on an inner surface of the second coating part relative to the light diffusion part.

6. The optical transfer device of claim 1, wherein:
   the optical probe comprises multiple optical elements provided on an end of a flexible wire or tube, as the light divergence part.

7. The optical transfer device of claim 1, wherein:
   the optical probe comprises a second light diffusion part having multiple second grooves formed on an end of an optical fiber wire, as the light divergence part.

8. The optical transfer device of claim 7, wherein:
   the refractive index of the first coating part is greater than the refractive index of a core of the optical fiber wire.

9. The optical transfer device of claim 7, wherein:
the second multiple grooves are formed by mechanically processing a core portion in which a clad is removed from an end of the optical fiber wire.
10. The optical transfer device of claim 7, wherein:
a core portion, in which a clad is removed from an end thereof, has a tapered shape.
11. The optical transfer device of claim 7, wherein:
a core portion, in which a clad is removed from the end thereof, has a shape comprising a ball shape which is additionally formed at the end of a tapered shape and has a large diameter.
12. The optical transfer device of claim 7, wherein:
a core portion, in which a clad is removed from the end thereof, has a cylindrical shape.
13. The optical transfer device of claim 7, wherein:
a core portion, in which a clad is removed from the end thereof, has a shape comprising a ball shape which is additionally formed at the end of a cylindrical shape and has a large diameter.

* * * * *